United States Patent [19]

Ayme

[11] 4,337,243
[45] * Jun. 29, 1982

[54] IMMUNOSTIMULANT MEDICAMENT AND PROCESS OF PREPARING SAME

[75] Inventor: Gérard Ayme, Lyons, France

[73] Assignee: Institut Merieux, S.A., Lyons, France

[*] Notice: The portion of the term of this patent subsequent to Jan. 8, 1997, has been disclaimed.

[21] Appl. No.: 71,591

[22] Filed: Aug. 30, 1979

Related U.S. Application Data

[63] Continuation-in-part of Ser. No. 804,150, Jun. 6, 1977, Pat. No. 4,182,751.

[30] Foreign Application Priority Data

Jun. 4, 1976 [FR] France ............................. 76 16937

[51] Int. Cl.³ ............................................. A61K 39/02
[52] U.S. Cl. ...................................................... 424/92
[58] Field of Search ........................................ 424/92

[56] References Cited

U.S. PATENT DOCUMENTS 3,636,192  1/1972  Gotschlich ........................... 424/72

Primary Examiner—Donald B. Moyer
Attorney, Agent, or Firm—Stevens, Davis, Miller & Mosher

[57] ABSTRACT

A new medicament which stimulates non-specific immunity and contains a phenol-soluble extract of microorganisms, wherein the phenol-soluble extract or fraction thereof of bacteria, yeasts and/or protozoa is rendered water soluble and free from endotoxin, substantially free from phenol and used in a portion for stimulating the receiving organism.

21 Claims, 4 Drawing Figures

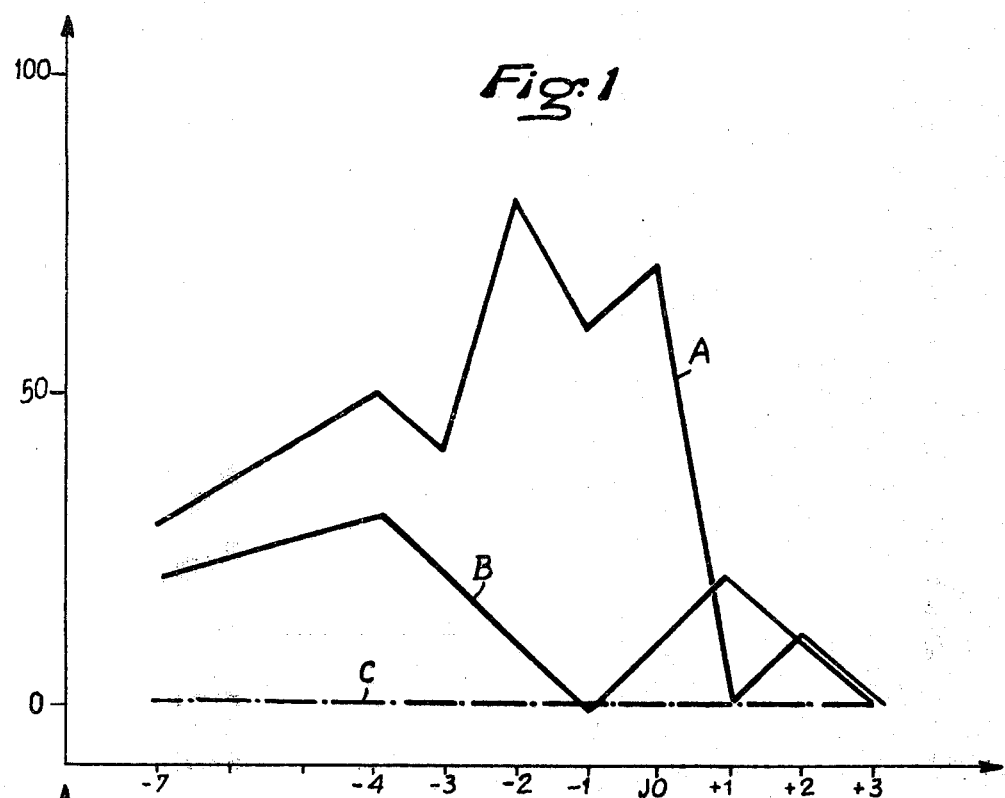
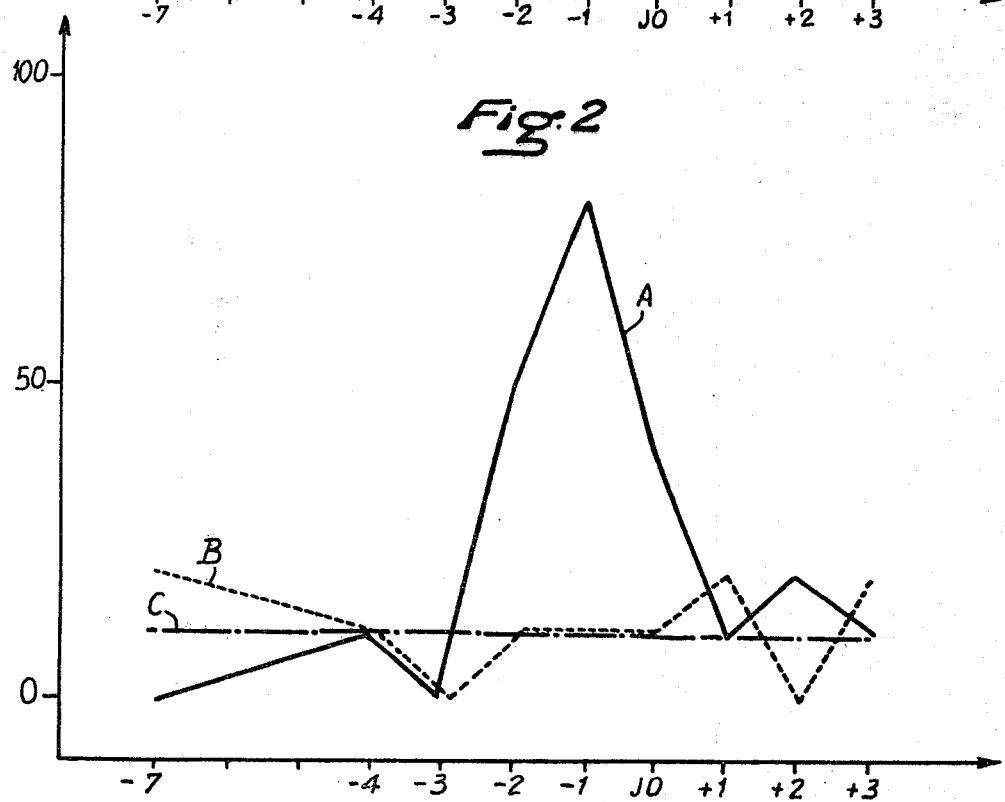

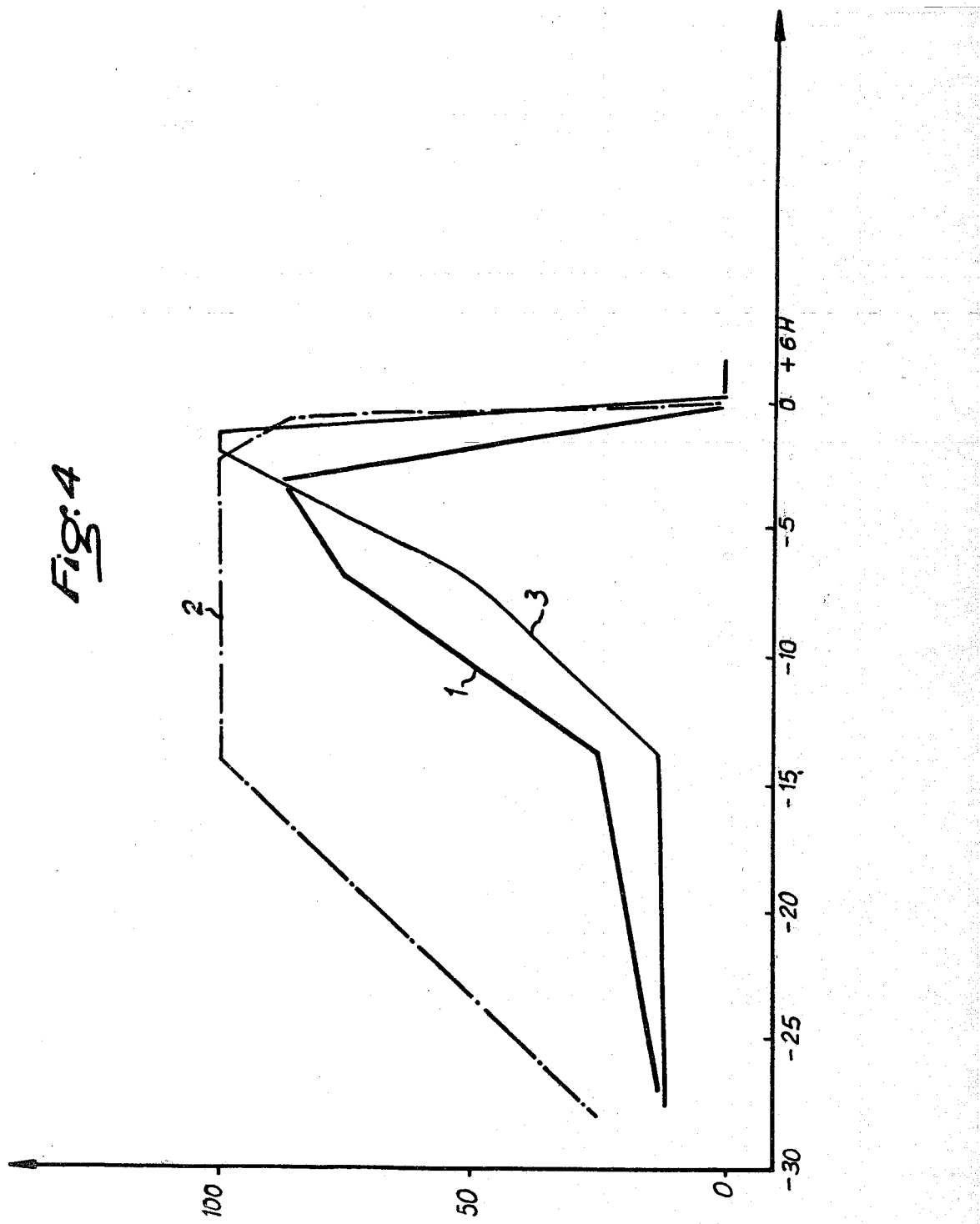

IMMUNOSTIMULANT MEDICAMENT AND PROCESS OF PREPARING SAME

This application is a continuation-in-part of U.S. patent application Ser. No. 804,150, filed on June 6, 1977, now U.S. Pat. No. 4,182,751 issued on Aug. 1, 1980.

BACKGROUND OF THE INVENTION

The present invention relates to a new medicament which is distinguished by its properties of stimulating non-specific immunity.

The invention likewise relates to a process for the preparation of this medicament.

The present invention is intended to furnish, as a new product, a medicament which stimulates non-specific immunity and which is represented by a purified extract of bacterial origin and of a proteinaceous and physicochemically defined nature.

It is already known, particularly from U.S. Pat. No. 3,483,290, that it is possible to obtain preparations that stimulate non-specific immunity, by phenol extraction of bacterial and particularly protoplasmic materials, particularly from *Escherichia coli*, this extract being freed from phenol by alcoholic precipitation. However, the described process does not permit sufficiently complete elimination of the lipopolysaccharide endotoxin, which gives rise to pyrogenic and toxic effects that prevent a true medicament from being obtained. It is true that the process of U.S. Pat. No. 3,483,290 seeks to limit contamination by the endotoxin by starting, in particular, from the protoplasm after grinding of the cells. This is not sufficient, however, to ensure a sufficient elimination, for the contamination persists even if the amount of endotoxin is relatively small.

Furthermore, this process concludes with an extract which is by definition insoluble in water. This prevents a sufficient final purification being obtained and prohibits the preparation of medicaments that can really be checked and sterilized.

The present invention thus proposes to go far beyond that teaching and to furnish a new, certain, practical medicament which can be monitored.

BRIEF SUMMARY OF THE INVENTION

This medicament offers to human medicine and also to veterinary practice a weapon which can be utilized in the very broad domain of the fight against infectious agents and in every case in which it is desired to increase the level of resistance of the immune defenses, for example against tumor states. It can likewise be associated with other means of fighting against attacks, for example to augment the activity of vaccines, to reinforce the activity of antibiotics while their dose levels are reduced, or to act synergistically with certain anti-tumor agents.

The toxicity possessed by this medicament is sufficiently low as to be negligible in efficacious doses and to permit repeated treatments.

Moreover, the medicament according to the invention has a high stability, which facilitates storage and use. It can be sterilized, for example, by filtration and/or heating.

Finally, the invention is intended to furnish a process for the manufacture of this medicament, said process having the advantage of being simple, or low cost, easy to carry out and able to be varied easily in numerous ways, so that high adaptability is obtained.

The object of the invention is a new medicament which stimulates non-specific immunity and which contains a phenol-soluble extract of micro-organisms, characterized by the fact that it comprises the phenol-soluble extract, or a fraction of this extract, of one or more of the unicellular microorganisms as follows: bacteria, yeasts and protozoa, said extract or fraction being rendered water-soluble and free from endotoxin and substantially free from phenol and portioned in a quantity stimulating the receiving organism.

DETAILED DESCRIPTION

Figure 3:
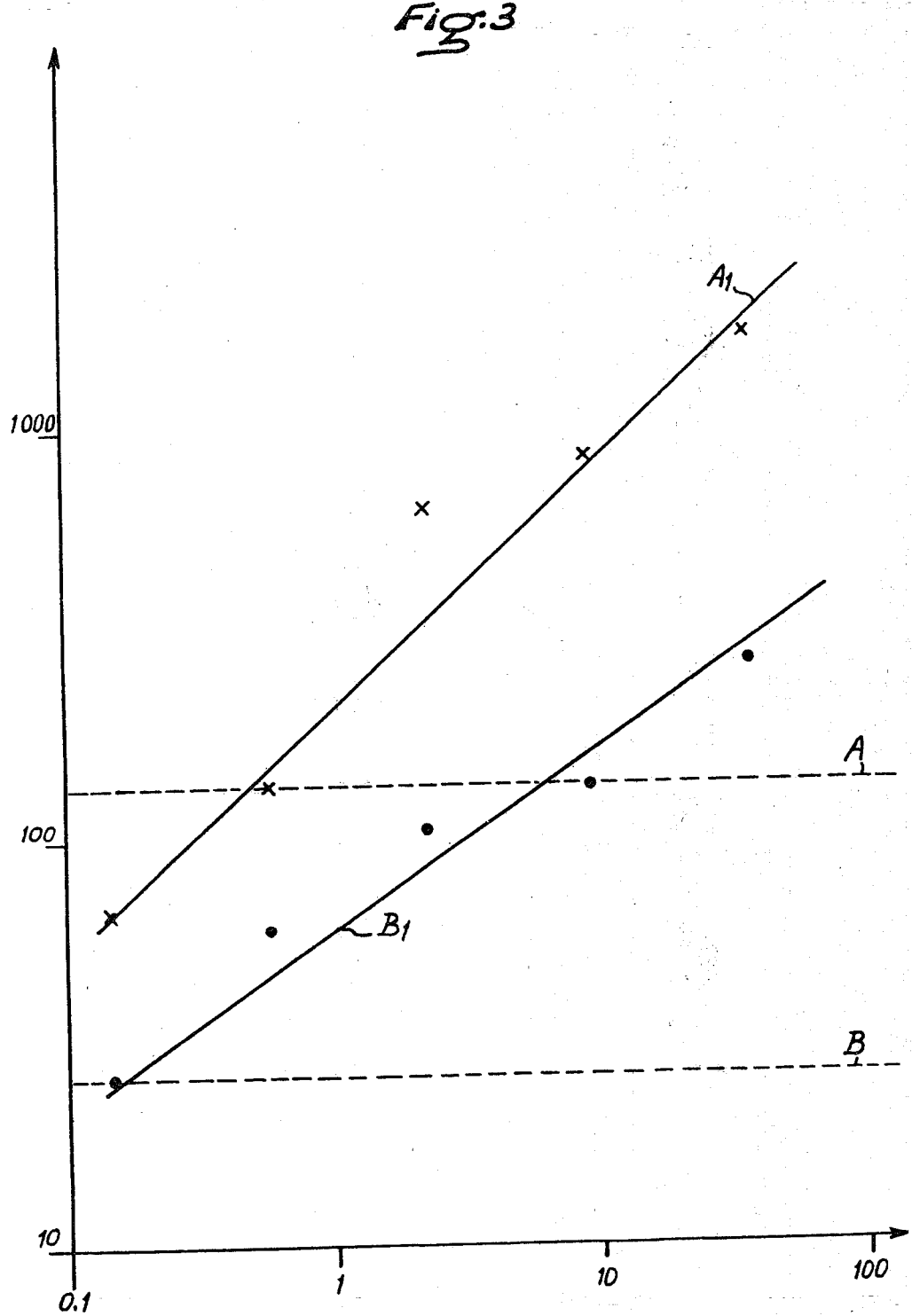

In a first embodiment, the medicament comprises an extract, or a fraction of an extract, which is phenol-soluble and derives from bacteria or from mycobacteria, yeasts or protozoa.

Among bacteria, there are preferred:
*Neisseria meningitidis, Proteus mirabilis, Bordetella pertussis, Klebsiella pneumoniae, Acinetobacter anitratus, Pseudomonas aeruginosa, Escherichia coli, Brucella abortus, Corynebacterium pseudodiphtheria, Corynebacterium parvum,* and *Staphylococcus aureus.*

In a particularly preferred manner, the medicament can comprise an extract, or fraction, of mycobacteria, and preferably of *Mycobacterium phlei, Mycobacterium kansasii, M. scrofulaceum, M. intracellulare,* or *M. fortuitum.*

In the case in which the medicament comprises a phenol-soluble extract of yeast, extracts of *Saccharomyces cerevisiae* are preferred.

The medicament according to the invention can be associated with other pharmaceutical products or compositions, such as *Corynebacterium parvum,* antibiotics, antimitotics, corticoids, vitamins, and likewise with various vaccines, for example against influenza, whooping-cough, polio-myelitis, measles, rubella, tetanus and diphtheria toxoids, and meningococcal polysaccharides, either singly or together.

The medicament according to the invention can be provided in various forms, for example in an injectable form, or for example in the form of a solution or suspension in saline or in an oily excipient or also one of oil in water or water in oil; in a lyophilized form or as an aerosol; in a drinkable form, or one which can be administered by the rectal route. It can advantageously comprise an adjuvant on which it if preferably absorbed, for example aluminum hydroxide.

The medicament can likewise be provided in the form of an ointment with the aid of a suitable usual excipient.

The doses to be administered depend on the affection to be treated, the nature of the treatment and of the organism undergoing the treatment. This dose can be left without difficulty to the judgment of the physician or of the veterinarian as is usually done, in a well-known manner, in treatments involving stimulation of immunity.

By way of example, the dose can comprise from 10 to 1,000 micrograms dry weight of extract, and for human treatment a suitable dose can be of the order of 400 micrograms.

The administration of the medicament can notably be carried out by an external route, for example in the form of an ointment or powder; by a subcutaneous, intradermal, parenteral, intraperitoneal, or intramuscular route; by inhalation in the form of an aerosol; or also by the oral or rectal route.

The medicament according to the invention is notably suitable for treatment, by stimulation of non-specific immunity, of burned or traumatized cases, or of organisms lacking immunological defenses. It can likewise be utilized in a preventive or curative manner in an infectious environment, for example, for common infections or to avoid complications subsequent to viral or tumoral affections.

An other object of the invention is to provide a method for treating or preventing infections, and, more generally, for stimulating non-specific immunity, which comprises administering to a human, or, more generally, to a vertebrate, an effective amount of the medicament of the invention.

Said method is particularly a method for treating or preventing bacterial infections particularly in immunodepressed man or animal.

The medicament according to the invention presents only a low toxicity, varying to a small degree as a function of the microorganism utilized, as is shown by the weight gain test with mice, the study of sensitizing power in the rabbit and the guinea-pig (Schwarzman reaction), and the tests of chronic toxicity in piglets, calves, and adult bovines.

The absence of hypersensitization in the Schwarzman test shows that the medicament is free from endotoxin.

Moreover, it is known that small doses of endotoxin can provide a stimulation of non-specific resistance to infections. It was shown that the medicament of the invention does not provide such a stimulation of non-specific immunity due to endotoxins.

In fact, the endotoxin content in the present medicament is at least about 1,000 times less than the minimal dose of endotoxin giving rise to a sensitization reaction.

This is why the medicament of the invention may be characterized as substantially free from endotoxin.

The medicament according to the invention acts in particular by the stimulation of the non-specific immune system. It has a considerable antibacterial activity as well as an anti-viral activity. It gives excellent protection against secondary bacterial infections during the course of a viral disease. It possesses an interferon-inducing power. It gives rise to a marked rise in the level of circulating heterologous antibodies.

It likewise possesses a considerable cellular activity. Phagocytosis is strongly stimulated, and there is noted an increased reaction of graft against host and a mitogenic effect, particularly on human lymphocytes.

The invention likewise has the object of a process of preparation of the medicament according to the invention, characterized by the fact that a microorganism such as a bacterium, yeast or protozoon is extracted by means of phenol which is liquid at the temperature of extraction, below 70° C. and after the phenol phase has been collected, this phenol is eliminated, and the extract is then rendered water-soluble.

Among the phenols there are preferred phenol itself, or possibly the cresols and particularly metacresol or 3-methyl-4-chlorocresol.

The temperature is preferably below 70° C. and preferably above 0° C. The operation can advantageously be carried out at a temperature between 60° and 67° C.

The duration of the extraction can be between several minutes and several hours. Preferably, it is between 30 minutes and 3 hours.

The quantity of phenol is relation to the quantity of water in the initial suspension can be arbitrary, for example, it can be between 15 and 85%. In other words, the extraction is carried out in the presence of water. However, it is preferred to utilize the proportion of phenol giving the most satisfactory emulsion. In the case of phenol ($C_6H_5OH$) itself, this preferred proportion is 45% phenol.

In the case of gram-negative bacteria, the extraction can be carried out directly on a bacterial suspension. In the case of gram-positive bacteria, or mycobacteria, a grinding or a bacterial lysis is preferably first carried out before proceeding to the extraction.

Preferably, the extraction is carried out in the presence of an anionic detergent such as sodium dodecylsulfate, for example. The effect of the presence of the detergent is to facilitate the operation and also to cause the disappearance of certain sensitizing activities, notably of endotoxins.

The choice of pH is not of great importance, but a suspension can be acted on with phenol at a substantially neutral pH, for reasons of simplicity.

The separation of the phenolic and aqueous phases can be effected conventionally, for example by centifugation or by direct separation, for example by means of a pipette, after decantation.

The separation of the phenolic and aqueous phases can advantageously be rendered easier and more complete by the addition of salts such as, for example, $MgCl_2$ or $NaCl$ at a high concentration. The salt can be added in the crystalline form or as a concentrated solution, and this addition can be made either at the first time of extraction or, after breaking of the phenol/water emulsion, to the already-decanted phenolic phase, in order to free it from the water of saturation. The phenolic phase obtained, clear and colored, can likewise be washed several times with water.

These operations enable practically all the endotoxins to be eliminated, even in the case of gram-negative bacteria such as *E. coli*, which are strongly contaminated.

Surprisingly, the process can be efficiently carried out by extraction within extremely broad limits of temperature, of concentration between the phenolic phase and the aqueous phase, of pH, and of ionic strength.

Furthermore, the positive results observed for the extracts of a large number of microorganisms tested within the scope of the present invention permit it to be thought that these extracts enable medicaments to be prepared whatever the strain of bacteria, mycobacteria, or yeasts, utilized.

After the extraction, the phenol is eliminated in order to recover the active material of a proteinaceous nature which is dissolved in the phenolic phase. Because of the great physicochemical stability of this extract, this elimination can be effected by numerous different means.

Thus, in a first manner of proceeding, an alcohol precipitation can be carried out, with recovery of the precipitate.

In a second manner of proceeding, the phenolic phase is treated by a precipitating agent such as, for example, polyethylene glycol in phenol solution. A first stage of purification can be obtained as a function of the concentration of polyethylene glycol, which permits the molecular population to be fractionated into different groups.

In a third manner of proceeding, the elimination of the phenol can be carried out by distillation under vacuum.

At the end of the different procedures cited above, the product obtained is practically free from phenol and insoluble in water. After washing and/or dialysis, if necessary, for elimination of the last traces of phenol, it can be resuspended and homogenized in water or in a buffer or in saline solution.

The product withstands a treatment of high temperature in an autoclave, for example, at +115° C. for 30 minutes, both in the form of an aqueous suspension and as a dehydrated lyophilisate.

The product is then subjected to a treatment to render it water-soluble and to further purify it.

Such a treatment can be carried out either by adding a surface active agent, particularly an anionic surface active agent, or by dialysis.

When water-solubilization is obtained by addition of a surface active agent, the excess surface active agent may be removed, e.g. by addition of potassium chloride which yields a precipitate of the potassium salt of an anionic surface active agent.

After water-solubilization, the product may be subjected to various purification steps, e.g. by treatment with adsorbing agents such as activated carbon, silica, clay or, preferably, baryum sulfate, or to various fractionation steps by usual methods, e.g. chromatography or by precipitating part of the solubilized product by an acidic agent lowering the pH, and eliminating the supernatant fluid.

The soluble and purified product obtained can advantageously be mixed with a finely particulate support, for example aluminum hydroxide, aluminum phosphate or calcium phosphate, or complexed to a macromolecule, for example, to a polycation such as methylated albumin or a DEAE dextran.

As indicated above, the water-solubilization steps may be carried out by dialysis. It is advantageous to carry out said dialysis on the phenol solution, which makes possible both elimination of phenol and water-solubilization. Said dialysis is carried out against water, or preferably, against an alkaline buffer for reasons of speed. If a residue persists it is eliminated, after which the water-soluble product collected can undergo one or several operations of purification and concentration, and possibly receive an adjuvant or a gel or be complexed with a macromolecule as mentioned above.

Other advantages and characteristics of the invention will become apparent to the reader of the following description, which is of a non-limitative nature.

I. EXTRACTION

EXAMPLE 01: Extraction with phenol

Ten grams of dry cells of bacteria or of yeasts are mixed with 350 ml of distilled water, and this mixture is brought to a temperature of 65° C. There are then added 315 ml of pure phenol, preferably previously heated to 65° C., and 35 ml of SDS (sodium dodecylsulfate), 6.66%, heated to 65° C. The final phenol concentration is 45% and that of SDS, 0.33%.

This mixture is stirred for an hour while being kept at the temperature of 65° C., then is cooled to between 0° and +4° C. and left at 4° C. overnight.

A lower phenol layer and an upper aqueous layer are obtained, with an intermediate phase comprising gross debris. The interphase and the aqueous phase are eliminated, and the decanted phenolic phase is preferably centrifuged at 35,000 g for an hour at +10° C. The interphase and the aqueous phase obtained are eliminated, and a clear colored phenolic phase is retained.

The same process of extraction can be utilized for all the microorganisms falling within the scope of the invention.

EXAMPLE 02: Extraction with metacresol

A suspension containing 10 g of dry germs in 500 ml of distilled water is heated to 37° C., then mixed with 500 ml of metacresol heated to 37°. After 3 minutes of stirring at 37° C., the mixture is centrifuged, and the aqueous phase and the interphase are eliminated.

EXAMPLE 03: Extraction with phenol

Ten grams of dry bacteria are mixed with 400 ml of distilled water and the temperature of the mixture is brought to 40° C. Then 350 ml of 90% phenol at 4° C. are added. The mixture is stirred for 6 hours at 4° C. and allowed to settle overnight at 4° C. The aqueous phase and the interphase are then eliminated by centrifugation.

EXAMPLE 04

Ten grams of dry germs are mixed with 350 ml of a 30% solution of NaCl and brought to 65° C. 315 ml of pure phenol, previously heated to 64° C., and 35 ml of a 0.2 M solution of SDS heated to 64° C. are added, and the mixture is stirred for 1 hour at this temperature, then cooled to 25° C.

On centrifugation there is then obtained an upper phenolic phase, which is decanted and mixed with an equal volume of non-pyrogenic distilled water at 25° C. and is stirred to form an emulsion for 25 minutes and is then centrifuged to break the emulsion and recover the phenolic phase thus washed, after decantation of the supernatant aqueous phase.

EXAMPLE 05: Extraction with phenol

The mixture is prepared as in Example 1 for 1 hour while being kept at the temperature of 65° C. The mixture is then cooled to 20° C., and enough crystallized NaCl is then added to bring the concentration of the aqueous phase to 30%, or about 115.5 g. The mixture is agitated for 30 minutes at +20° C., and is then centrifuged, and the supernatant phenolic phase is recovered.

II. ELIMINATION OF THE PHENOL

EXAMPLE 1

The phenolic phase obtained in Example 01 above is mixed with 5 volumes of methanol, precooled to −20° C. There can advantageously be added 0.01 volume of a saturated methanolic solution of sodium acetate.

The mixture is then kept for several hours, for example overnight, at low temperature, for example, 4° C.

The supernatant methanolic phase is than decanted, and the sediment is centrifuged at 15,000 g for about 30 minutes.

The pellet can be preserved as it is, to undergo a treatment of solubilization and precipitation, either later or immediately. It can be lyophilized, which permits elimination of phenol to be completed and the material to be kept in the dry state for long periods. The suspension or the lyophilizate can be heated in the autoclave.

The pellet can also be washed or dialyzed to eliminate the residual phenol and, for example, may be taken up in saline solution, pyrogen-free water, etc. It is, for example, taken up in distilled water to the amount of twice the volume of the phenolic phase treated and then dialyzed with agitation, against 50 volumes of distilled water at +4° C., for several hours, for example a night.

This dialysis is then repeated a second time against saline solution buffered to pH 7. A fraction S is finally obtained, insoluble in water. This fraction S can be sterilized by heating in an autoclave, for example at 115° C. for 30 minutes.

EXAMPLE 2

To the above fraction S, or to the pellet simply resuspended in water, dispersed in 1 volume of water at a concentration of 4 to 5 milligrams of protein per ml, 0.1 ml of 0.2 M SDS is added dropwise and with stirring, at ambient temperature, to dissolve the fraction.

Stirring is continued until complete dissolution, upon which 0.5 volume of an 18.75% suspension of $BaSO_4$ in water is added. After 2 hours of stirring at ambient temperature, the mixture is centrifuged at 15,000 g for 30 minutes. The pellet is eliminated and 0.05 volume of saturated KCl is added to the supernatant fluid, in order to eliminate the dodecylsulfate, which precipitates. After further centrifugation at 15,000 g for 30 minutes, the pellet is discarded and the clear supernatant fluid is collected. This is dialyzed against saline solution buffered to pH 7, in an amount of 3 times 50 volumes, until the elimination of the residual phenol and of the residual KCl.

A final filtration on Millipore filters, first $0.45\mu$ and then $0.22\mu$, gives the fraction SS which, in contrast to the fraction S, is soluble.

Preferably, an adjuvant, such as alumina, another gel, DEAE dextran, or a methylated albumin, is added to this fraction.

EXAMPLE 3

The phenolic phase obtained by extraction according to Example 01 is dialyzed against distilled water, with agitation of the dialysis tubing, until the phenol is eliminated; this requires three dialyses each using 50 volumes.

A dialysis is then carried out against sodium phosphate buffer at pH 8, at room temperature and with agitation of the tubing, until dissolution occurs. This dialysis is carried out twice with 50 volumes.

The total duration of the dialyses is several hours, for example, about 48 hours.

If there is a residue, centrifugation is carried out at 15,000 g for 30 minutes, and the residue is eliminated. However, for a large number of bacteria, no residue is seen.

The clear supernatant fluid is dialyzed against saline solution buffered to pH 7, using 50 volumes for each of two dialyses. There is obtained a fraction SSp, still more active than the above fraction SS.

The purification can be continued by lowering the pH to 4 with HCl during agitation; this gives rise to a precipitate. After centrifugation at 15,000 g for 30 minutes, the supernatant fluid is discarded.

The precipitate is taken up again in distilled water, 1 volume per volume of precipitate resulting from the reduction of pH, and a dialysis is then carried out against saline solution buffered to pH 7, until complete dissolution during three operations using 50 volumes each.

A fraction designated SSph is thus obtained, as a solution.

EXAMPLE 4

The phenol extract obtained according to Example 1 undergoes a precipitation by addition of polyethylene glycol of molecular weight between 1,500 and 20,000 and preferably of the order to 6,000.

The precipitate is then centrifuged and collected. It is then resuspended in water or preferably in saline solution.

The fractions obtained all have the same activity and are not soluble. They can, however, be rendered soluble by procedures analogous to those of Examples 2 and 3.

EXAMPLE 5: Extract of a protozoan 40 ml of a suspension of Toxoplasma gondii containing 443.6 mg of dry material were heated to 65° C. There were added 36 ml of pure phenol (heated at 65° C.) and 4 ml of a 6.66% aqueous solution of sodium dodecyl sulfate (SDS). The concentration of phenol was 45% and the concentration of SDS was 0.33%.

The mixture was agitated for 1 hour at 65° C. and then cooled to 15° C.

After centrifugation 34.5 ml of a phenolic phase were obtained to which 5 volumes of methanol at 4° C. were added in the presence of 0.01 volume of a methanolic solution saturated at 4° C. with sodium acetate.

The precipitate was collected by centrifugation and suspended into 20 ml of distilled water. The suspension was dialyzed against water until total elimination of the remaining phenol, methanol and sodium acetate.

The complete solubilization of the fraction was obtained by adding SDS up to a concentration of 0.33%.

The excess of SDS was precipitated in the form of its potassium salt by addition of a saturated aqueous KCl solution. The precipitate was eliminated by centrifugation and the supernatant was dialyzed until complete elimination of excess KCl.

The clear solution which was obtained had a U.V. spectrum typical of proteins, with a maximum at 276 nm and a ratio (O.D. 276 nm)/(O.D. 260 nm)=1.35 which showed that contamination with nucleic acids was absent or very low.

The extract was injected to mice at a dosage of 200 $\mu$g. The mice thus treated showed a significant resistance against infections induced with *Salmonella typhic* and *Escherichia Coli*.

EXAMPLE 6: Extraction of a yeast

To 400 ml of a suspension of *Candida albicans* containing 5.98 g of dry material, there were added phenol up to 45% and SDS up to 0.33%, and the mixture was agitated for 1 hour at 65° C.

The phenolic phase (350 ml) obtained after decantation and centrifugation was treated with 5 volumes of methanol precooled to $-20°$ C., in the presence of a methanolic solution saturated with sodium acetate.

The mixture was maintained at $+4°$ C. for 16 hours. The precipitate was collected by centrifugation and suspended into 80 ml of distilled water. The suspension was dialyzed against distilled water at $+4°$ C.

Solubilization of the proteins was then effected by adding SDS up to a concentration of 0.33%. The excess of SDS was precipitated with a saturated solution of KCl.

After centrifugation, the supernatant fluid was subjected to several ultrafiltration steps on membranes allowing elimination of all small molecules having a molecular weight lower than 10,000, including KCl.

The extract thus obtained had the typical U.V. Spectrum of proteins, with a maximum at 276 nm, and a ratio (O.D. 280 nm)/(O.D. 260 nm) largely greater than 1.

The nitrogen content was 15.7% (calculated on dry material), and 96% of the nitrogen was precipitable with trichloroacetic acid and thus a member of macromolecules. The content of proteins was 100% of the dry material in the LOWRY Test. The extract contained less than 1% of materials such as sugars, Ribonucleic acids, desoxyribonucleic acid and lipids.

The extract was injected to mice at a dosage of 200 μg. The mice thus treated showed a significant resistance against infections induced by *Salmonella typhi*, *Escherichia coli* and *Staphylococcus aureus*.

In order to provide evidence of the activity in non-specific stimulation of immunity, a large number of mice has been subjected to severe tests of bacterial infections, using as test bacteria Salmonella, Pseudomonas, *Escherichia coli*, Staphylococci, *Neisseria meningitidis* serogroup A, B and C, *Klebsiella pneumoniae*, and *Brucella abortus*.

In Table I below 50% protective doses of various extracts of 12 different origins, before heating and after heating at 115° for 30 minutes are set forth. The test organism was Salmonella.

Table II following below shows the cumulative results obtained with different extracts of Neisseria and of Proteus, expressed in percentage survival, for different doses per mouse in micrograms dry weight.

Table III following below shows the results, as a function of the doses administered to mice, of the protection afforded by extracts according to the invention against tests with Neisseria meningitidis serogroup A, B and C.

By way of example, a graph is shown in FIG. 4, the abscissa showing the time interval between the stimulation and the challenge and the ordinate showing the percentage of survival. The doses are administered to the mice by the intraperitoneal route.

Curve 1 shows the kinetics in mice stimulated by 50 micrograms of extracts S of Meningo M 21 in the course of a Salmonella test. Curve 2 shows the kinetics connected with a stimulation of 10 micrograms of extracts SS with Al adjuvant of Meningo M 29 against a Staphylo test.

Curve 3 shows the kinetics connected with a stimulation of 10 micrograms of extracts SS+Al of Pertussis Bp for a Staphylo test. It can be seen that the stimulation is established in one day, attains its highest level in two to three days, and stays significant during two to three weeks.

Table IV shows the results obtained for extracts of Neisseria and of Proteus as a function of the period between the administration to the mouse of the extracts according to the invention and the later challenge with N. meningitidis serogroup A, B and C.

Table V shows the results obtained with a stimulation by an extract SS+aluminum hydroxide, of Neisseria, at the beginning, as a single stimulation, followed by a Salmonella test three days later and a Pseudomonas test 17 days later, as well as after a multiple stimulation at 0, 7, 15, 21 and 28 days and a Salmonella test at the third, tenth and eighteenth day, then Pseudomonas the 24th day and coli on the 31st.

Table VI shows the protection against mixed tests afforded by the Neisseria extract. The test agent was constituted by a mixture of four bacterial species: Salmonella, Pseudomonas, Staphylococci, and coli.

The effect of repeated stimulation is shown in Table VII.

Table VIII shows the results obtained after protection by Neisseria extract against EMC virus tests (mouse encephalomyocarditis virus) and SF virus tests (Semliki-Forest virus).

In the same way, it has been possible to establish, for the medicaments according to the invention, a considerable protective activity against a secondary bacterial infection in the course of a viral infection. The trial was carried out on mice subjected to a viral test and receiving a LD50 dose, and subjected three days later to a bacterial test at a dose greater than a minimal lethal dose.

Table IX shows the activity of a Neisseria extract against secondary bacterial infection during the course of an EMC virus infection, the large arrow representing the data of administration of the medicament and the small arrow representing the date of administration of the test agent, in the first case EMC alone, in the second case coli alone, and in the third case a double test with EMC and then coli.

It is observed that a single injection of Neisseria extract SS before or after the viral infection gives excellent protection.

The tests, carried out on more than 20,000 mice, have shown that the mice stimulated by the medicament according to the invention showed good resistance in spite of the severity of the tests. The most efficacious medicaments were found to be those containing extracts of Neisseria and of Proteus and, to a lesser extent, Klebsiella.

The excellent activity of the extracts of *Neisseria meningitidis* has likewise been confirmed on various experimental models, with the use of large animals, pigs and bovines. These extracts have, for example, been able to protect the pig against a Rouget test sufficient to cause, in non-stimulated controls, generalization of the lesions.

Generally speaking, the best results were obtained for the SS fractions and occasionally for the SSp fractions.

The immunostimulant activity was markedly increased by use of an adjuvant such as $Al_2O_3$, $AlPO_4$, latex, aerosil, DEAE dextran, or a methylated albumin.

The trials also showed that a certain degree of antiviral stimulation was obtained. Thus, for example, the Neisseria extract, in a dose of 5 micrograms per mouse via the intranasal route, protects 8 mice out of 10 against influenza virus, and likewise by the aerosol route.

FIG. 1 shows a graph with the abscissa showing the number of days between the stimulation and the EMC virus test and the ordinate showing the percentage of survival. Curve A corresponds to mice which received by the intraperitoneal route a dose of 225 micrograms of Neisseria extracts and 150 micrograms of aluminum hydroxide. Curve B shows controls which received, instead of the stimulation, only 150 micrograms of aluminum hydroxide given intraperitoneally, and Curve C shows the controls which were given a simple administration of physiological water.

FIG. 2 is a graph, similar to that of FIG. 1, for an administration by the subcutaneous route.

In models of tumor affections in mice, it has also been established that there is a synergistic action of the association of the medicaments prepared according to the invention and certain anti-tumor agents, for example *Corynebacterium parvum;* a synergism which is particularly notable when the treatment using such an association is instituted as a curative measure.

It has also been possible to establish that the medicaments according to the invention ensured a non-specific stimulation of the heterologous circulating antibodies as well as a stimulation of the number of secretory lymphoid cells. From the point of view of cellular activity, there is obtained a stimulation of phagocytosis, a stimulation of the organs of the reticulo-endothelial system, an exacerbation of the reactions of delayed hypersensitivity in the guinea-pig, an exacerbation of the graft-versus-host reaction, and a stimulation of the synthesis of DNA in human lymphocytes activated in vitro.

FIG. 3 shows graphically the adjuvant effect obtained in the mouse against anti-influenza antibodies after immunization by a bivalent A and B influenza vaccine. The abscissa gives the logarithm of the does in micrograms of Neisseria extract with aluminum hydroxide, and the ordinate gives the logarithm of the IHA titer. Curve A shows the effect of valence A influenza vaccine without adjuvant, while Curve $A_1$ shows the case of this vaccine with the extract according to the invention as adjuvant.

Curve B corresponds to the valence B vaccine without adjuvant, and Curve $B_1$ to the valence B vaccine with adjuvant.

Generally speaking, the different fractions S, SS, SSP, SSH, SSpH all show a high level of activity.

In most cases it will thus be preferred to utilize the SS extract, the innocuousness and sterilization of which are easier to monitor than those of the S extract, which furthermore is not soluble, and the manufacture of which extract (SS) is easier than that of the SSp and SSH extracts.

The medicament according to the invention is preferably adsorbed on an adjuvant, preferably alumina, and it is preferably lyophilized.

In the dessiccated form, it can be advantageously heated in an autoclave, for example to 115°, permitting further a clear attenuation of the toxic reactions which could persist.

TABLE I

50% PROTECTIVE DOSES (DP 50) OF VARIOUS EXTRACTS EXPRESSED IN μG DRY WEIGHT PER MOUSE AGAINST A SALMONELLA TEST

| Origin | S | SS | SS + Al | SSp | SSp + Al |
|---|---|---|---|---|---|
| Neisseria meningitidis | 14,4 (125,3) | 112,2 (167,1) | 7,1 (14,1) 176,4 | (392,7) | 26,2 (57,0) |
| Proteus mirabilis | 15,8 (107,1) | 194,1 (210,4) | 7,6 (14,8) 65,3 | (111,8) | 14,7 (9,0) |
| Klebsiella pneumoniae | 76,4 (130,8) | 495,4 | 10,6 (7,2) | | (90,8) |
| Staphylococcus aureus | 25,1 | | 37,8 (25,1) | 26,2 | |
| Bordetella pertussis | 72,5 | 423,8 | 40 | | |
| Moraxella | 75,0 (165,2) | | (30,3) | | |
| Pseudomonas aeruginosa | (631,5) | (318,2) | 62,2 (141,1) | | |
| Brucella abortus | 110,7 | 286,5 | 90,8 (198) | | |
| Escherichia coli | 319,4 (165,2) | 413 (795,6) | 96,1 (118,8) 625 | 134 | |
| Mycobacterium phlei | (265,5) | | | | |
| Corynebacterium diphteriae | 252,2 | >225 | >225 | | |
| Corynebacterium parvum | | (230,3) | (67,3) | | | in parentheses: DP 50 of the extract after heating at 115° C. for 30 minutes.

TABLE II salmonella test
RESULTS (CUMULATIVE) OBTAINED WITH TYPES OF EXTRACTS SELECTED FOR THEIR IMMUNOSTIMULATING ACTIVITY

MOUSE DOSES IN μG DRY WEIGHT

| Origins Fraction | 225 | 112,5 | 75 | 40 | 25 | 20 | 10 | 8,3 | 5 | 2,5 | 0,9 | DP 50 |
|---|---|---|---|---|---|---|---|---|---|---|---|---|
| Neisseria SS + Al Survivors/Tested | 90/96 | 16/16 | 295/328 | 12/16 | 332/435 | | | 213/350 | | 65/112 | 7/32 | 7,07 |
| % survival | 93,8 | | 89,9 | | 76,3 | | | 60,9 | | 58 | 21,9 | |
| SS + Al S/E | 46/64 | | 341/420 | 10/16 | 311/515 | 23/32 | 103/228 | 167/376 | 77/148 | 5/48 | | 14,09 |
| heated 115° C. 30 mn | 71,9 | | 81,2 | | 60,4 | | 45,2 | 44,4 | 52 | 10,4 | | |
| Proteus SS + Al S/E | 8/8 | | 23/24 | | 27/32 | | | 13/24 | | 3/8 | | 7,58 |
| | | | 95,8 | | 84,4 | | | 54,2 | | | | |
| SS + Al S/E | | | 20/24 | | 40/56 | | 33/48 | 11/40 | 26/56 | | | 14,79 |
| heated % | | | 83,3 | | 71,4 | | 68,8 | 27,5 | 46,4 | 23.7 | | |
| SSp + Al S/E | 7/8 | 8/8 | 20/24 | | 44/56 | | 29/48 | | | 14/32 | | 14,72 |
| | | | 83,3 | | 78,6 | | 60,4 | | | 43,8 | | |

Non-stimulated controls = % survival = 1,7 %

TABLE III

PROTECTION AGAINST N. MENINGITIDIS SEROGROUP A, B AND C

| Origin | N° | of lot | Extract | Mouse dose in 225 | 75 | μg Route: SC 25 | 15 | 3 | Test Serogroup | Number | Route: IP DL50 SURVIVAL |
|---|---|---|---|---|---|---|---|---|---|---|---|
| Neisseria | A | MA 32 | S | | | 1 | 0 | 0 | A | 150 | 0 |
| | | | SS | | | 6 | 2 | 0 | | | |
| | | | SS + Al | | | 7 | 5 | 0 | | | |
| | | | Al | | | 0 | 0 | 1 | | | |
| Neisseria | A | MA 34 | SS + Al | | 5/9 | 3 | 1 | | A | 250 | 0 |
| Proteus | | Pm 03 | SS + Al | | 6/9 | 5 | 2 | | | | |
| | | | Al | | 0/9 | 0 | 1 | | | | |
| Neisseria | A | MA 30 | S | | | 7 | | | B | 100 | 0 |

TABLE III-continued

PROTECTION AGAINST N. MENINGITIDIS SEROGROUP A, B AND C

| Origin | N° of lot | Extract | Mouse dose in 225 | 75 | µg Route: SC 25 | 15 | 3 | Test Serogroup | Number | Route: IP DL50 | SURVIVAL |
|---|---|---|---|---|---|---|---|---|---|---|---|
| | | SS + Al | | 9 | | | | | | | |
| Neisseria C | MC 31 | S | | 8 | | | | | | | |
| | | SS + Al | | 7 | | | | | | | |
| Neisseria A | MA 30 | S | | 8 | | | | C | 50 | | 0 |
| | | SS + Al | | 15/20 | | | | | | | |
| | | Al | | 1/20 | | | | | | | |

Number of surviviors per 10 tested (unless otherwise indicated)

TABLE IV

PROTECTION AGAINST N. MENINGITIDIS, Sgp A, B AND C BY EXTRACTS SS + Al OF NEISSERIA AND PROTEUS HEATED 115° C. 30 minutes) (KINETIC)

Test Route: IP

| | | | | PERIOD OF STIMULATION ROUTE: SUBCUTANEOUS | | | | | | | | |
|---|---|---|---|---|---|---|---|---|---|---|---|---|
| | | | | 7 DAYS | | | 14 DAYS | | | 21 DAYS | | |
| Origin | N° LOT | N. meningitidis Type of extract | Serogroup Doses/mouse | A % OF SURVIVAL | B | C | A % OF SURVIVAL | B | C | A % OF SURVIVAL | B | C |
| Neisseria | MA 34 | SS + Al | 200 µg + 100 µg Al | 100 | 50 | 90 | 30 | 10 | 0 | 30 | 0 | 10 |
| | | | ⅓ | 80 | 30 | 20 | 10 | 20 | 10 | 10 | 10 | 10 |
| | | | 1/9 | 30 | 0 | 0 | 0 | 10 | 0 | 0 | 0 | 0 |
| Proteus | Pm 03 | SS + Al | 200 + 100 | 70 | 0 | 30 | 20 | 0 | 10 | 10 | 20 | 10 |
| | | | ⅓ | 20 | 0 | 10 | 10 | 0 | 10 | 0 | 0 | 0 |
| | | | 1/9 | 30 | 0 | 0 | 0 | 0 | 10 | 10 | 10 | 0 |
| | | Al | 100 µg | 0 | 0 | 0 | 20 | 0 | 0 | 10 | 0 | 0 |
| | | | ⅓ | 10 | 10 | 0 | 0 | 0 | 0 | 0 | 0 | 0 |
| | | | 1/9 | 0 | 0 | 0 | 10 | 0 | 10 | 0 | 10 | 10 |

| TESTS | A | 3500 germs | 120 LD 50 | 0% Survival |
|---|---|---|---|---|
| | B | 400 germs | 40 LD 50 | 0% Survival |
| | C | 1200 germs | 10 LD 50 | 0% Survival |

TABLE V

PROTECTION AGAINST SUCCESSIVE TESTS BY EXTRACT SS + Al OF NEISSERIA (J = DAY)

| single STIMULATION | | Stimulation J0 30 µg 10 µg 3,3 µg | Test: Salmonella J3 14 14 6 | Test: Pseudomonas J17 14 14 Number of survi- 6 vors per 16 tested Controls = 0/16 |
|---|---|---|---|---|

| STIMULATION MULTIPLE | Stimulation Tests | J0 | J7 | J15 | J21 | J28 | |
|---|---|---|---|---|---|---|---|
| | | J3 Salmonella | J10 Salmonella | J18 Salmonella | J24 Pseudomonas | J31 Coli | |
| Dose/mouse | 30 µg | 8 | 8 | 8 | 7 | 7 | |
| | 10 µg | 5 | 5 | 5 | 4 | 4 | |
| | 3,3 µg | 4 | 4 | 4 | 1 | 1 | |

Number of survivors per 8 tested    Controls 0/8

TABLE VI

PROTECTION AGAINST MIXED TESTS (Mixture of 4 bacterial species) BY EXTRACT SS + Al OF NEISSERIA (J = DAY)

| Stimulation | | J0 | J0–J7 | J0 | J0–J7 | J0 | J0–J7–J14 | J0–J7–J14–J21 |
|---|---|---|---|---|---|---|---|---|
| Test | | J10 | J10 | J3–J10 | J3–J10 | J17 | J17 | J24 |
| | 25 µg | 8 | 8 | 8 | 7 | 7 | 8 | 8 |
| Doses/mouse | 8,3 µg | 4 | 5 | 4 | 2 | 2 | 8 | 5 |
| | 2,7 µg | 0 | 0 | 0 | 3 | 1 | 4 | 1 |

Number of survivors per 8 tested    Controls 0/8

TABLE VII

EFFECT OF REPEATED STIMULATIONS
(EXTRACT SS + Al OF NEISSERIA - SALMONELLA TEST)

| Number of stimulation | Period between each stimulation | Doses/mouse = | Test 10 days after the last stimulation | | | Test 17 days after the last stimulation | | |
|---|---|---|---|---|---|---|---|---|
| | | | 75 μg | 25 | 8,3 | 75 | 25 | 8,3 |
| 1 | | | 8 | 8 | 2 | 7 | 5 | 0 |
| 2 | 7 days | | 8 | 8 | 7 | 7/7 | 6 | 6 |
| 2 | 14 days | | 8 | 8 | 6 | 8 | 7 | 6 |
| 3 | 7 days | | 15/16 | 16/16 | 12/15 | 8 | 4 | 3 |
| 3 | 14 days | | 15/16 | 14/15 | 15/16 | 6 | 6/7 | 4 |

Number of survivors per 8 tested (unless otherwise indicated)
Controls : 0/8

TABLE VIII

PROTECTION AGAINST VIRUS TESTS BY EXTRACTS OF NEISSERIA

| TEST | EMC ROUTE: SC | | | EMC ROUTE: IP | | | SF ROUTE: SC | | |
|---|---|---|---|---|---|---|---|---|---|
| Route of stimulation | SC | IP | IV | SC | IP | IV | SC | IP | IV |
| Period in days before test | 1-4 | 1-4 | 1-4 | 1-4 | 1-4 | 1-4 | 1-4 | 1-4 | 1-4 |
| S | 60-70 | 25-10 | 65-20 | 90-40 | 90-10 | 60-10 | 80-40 | 10-10 | 60-10 |
| SS | 40-30 | 30-0 | 60-20 | 70-70 | 100-0 | 30-10 | 60-60 | 20-0 | 40-10 |
| SS + Al | 70-50 | 30-10 | 55-0 | 50-30 | 80-0 | 30-10 | 80-70 | 10-0 | 60-20 |
| Control Al | 45-20 | 5-10 | 15-10 | 20-30 | 30-10 | 40-0 | 20-30 | 20-20 | 40-0 |
| Control H20 | 5-20 | 5-20 | 5-20 | 10-10 | 10-10 | 10-10 | 0-0 | 0-0 | 0-0 |

Results expressed in % survival

TABLE IX

PROTECTION AGAINST BACTERIAL SECONDARY INFECTION DURING COURSE OF A VIRAL INFECTION
(Cumulative of 2 experiments)

| (J = DAY) | Survivors Tested | % of Survival |
|---|---|---|
| Protection against EMC (J0) | 7/20 | 35% |
| EMC Test: M 29 at J-3, EMC at J0 | 10/20 | 50% |
| EMC at J0, M 29 at J1 | 14/20 | 70% |
| Protection against Coli (J3) | 0/40 | 0% |
| Coli test: M 29 at J-3, Coli at J3 | 36/40 | 90% |
| M 29 at J1, Coli at J3 | 36/36 | 100% |
| Protection against EMC (J0) then Coli (J3) | 3/60 | 5% |
| Double test: M 29 at J-3, EMC at J0, Coli at J3 | 52/60 | 86,7% |
| EMC then Coli | | |

TABLE IX-continued
PROTECTION AGAINST BACTERIAL SECONDARY INFECTION DURING COURSE OF A VIRAL INFECTION
(Cumulative of 2 experiments)

| (J = DAY) | | | | Survivors Tested | % of Survival |
|---|---|---|---|---|---|
| | EMC | M 29 | Coli | 60/60 | 100% |
| | J0 | J1 | J3 | | |
| M 29 | EMC | M 29 | Coli | 39/40 | 97,5% |
| J-3 | J0 | J1 | J3 | | |

What is claimed is:

1. A medicament stimulating nonspecific immunity in a subject, obtained by:
   (a) extracting an aqueous suspension of a member selected from the group of unicellular whole bacteria, and ground bacteria with a liquid phenol, in the presence of water, at a temperature below 70° C.;
   (b) collecting the phenol phase;
   (c) eliminating said phenol to leave a substantially phenol-free bacterial extract; and
   (d) rendering said extract water-soluble;
   wherein said medicament is substantially free of endotoxin and of phenol.

2. A medicament according to claim 1, wherein said extract is of a bacterium selected from the group consisting of: *Neisseria meningitidis, Proteus mirabilis,* and *Klebsiella pneumoniae.*

3. A medicament according to claim 1, wherein said extract is of a bacterium selected from the group consisting of: *Bordetella pertussis, Acinetobacter anitratus, Pseudomonas aeruginosa, Escherichia coli, Brucella abortus, Corynebacterium pseudodiphtheriae, Corynebacterium parvum, Staphylococcus aureus.*

4. A medicament according to claim 1, wherein said extract is of mycobacteria.

5. A medicament according to claim 4, wherein said extract, or fraction, is of a mycobacterium selected from the group consisting of: *Mycobacterium phlei, Mycobacterium kansasii, Mycobacterium scrofulaceum, Mycobacterium intracellulare,* and *Mycobacterium fortuitum.*

6. A medicament according to claim 1, wherein the extraction is carried out in the presence of an anionic detergent.

7. A medicament according to claim 1, wherein the separation of the phenolic and aqueous phases is facilitated by addition of salt at a high concentration.

8. A medicament according to claim 1, wherein the phenol is eliminated by alcohol precipitation, and the precipitate thus obtained is collected.

9. A medicament according to claim 8, wherein said precipitate is then taken up again in distilled water and then dialyzed against water.

10. A medicament according to claim 1, wherein, in view of eliminating phenol, the phenolic extract is submitted to a precipitation by addition of polyethylene glycol, and the precipitate thus obtained is collected.

11. A medicament according to claim 1, wherein the phenolic phase is evaporated under vacuum to eliminate the phenol.

12. A medicament according to claim 1, wherein the phenol is eliminated by dialysis.

13. A medicament according to claim 12, wherein the dialysis is carried out against water or against an alkaline buffer.

14. A medicament according to claim 12, wherein the phenol is eliminated, and the extract is water-solubilized, by dialysis.

15. A medicament according to claim 1, wherein the aqueous solution which is obtained is then submitted to the action of an adsorbing agent.

16. A medicament according to claim 1, wherein the extract is submitted to a fractionation.

17. A medicament according to claim 1 wherein step (d) is accomplished by dissolving said extract in water in the presence of a surface active agent.

18. A medicament according to claim 17, wherein said surface active agent is anionic.

19. A medicament according to claim 18, wherein the excess of anionic surface active agent is then eliminated by adding a soluble potassium salt and eliminating the precipitate thus obtained.

20. A medicament according to claim 1 wherein said step (d) is accomplished by dialysis.

21. A medicament according to claim 20 wherein said dialysis is carried out against water or against an alkaline buffer.

* * * * *